United States Patent
Marchi et al.

Patent Number: 5,480,650
Date of Patent: Jan. 2, 1996

[54] PROGRAMMED RELEASE TABLETS CONTAINING NAPROXEN

[75] Inventors: Egidio Marchi; Leone G. Rotini, both of Bologna, Italy

[73] Assignee: Alfa Wassermann S.p.A., Alanno, Italy

[21] Appl. No.: 115,897

[22] Filed: Sep. 1, 1993

[30] Foreign Application Priority Data

Sep. 11, 1992 [IT] Italy .................. BO92A0315

[51] Int. Cl.⁶ ..................................... A61K 9/20
[52] U.S. Cl. .................. 424/464; 424/489; 424/468; 424/470
[58] Field of Search .................. 424/464, 468, 424/472, 470, 489

[56] References Cited

U.S. PATENT DOCUMENTS 4,888,178 12/1989 Rotini et al. .................. 424/468
5,204,116 4/1993 Edgren et al. .................. 424/472
5,232,705 8/1993 Wong et al. .................. 424/473

*Primary Examiner*—Thurman K. Page
*Assistant Examiner*—William E. Benston, Jr.
*Attorney, Agent, or Firm*—Bucknam and Archer

[57] ABSTRACT

Programmed release tablets, to be administered by oral route, containing from 500 to 1,200 mg of naproxen, made by mixtures of an immediate release granulate dry compacted containing from 5% to 28% of naproxen, of a controlled release granulate dry compacted containing from 72% to 95% of naproxen and of a disintegrating agent. A portion of naproxen is released in a short time, so that the drug can quickly develop its therapeutic action reaching the necessary hematic levels, while the remaining portion is released in a longer interval of time, so as to allow the therapeutic coverage until the subsequent administration. The therapeutic coverage is effective for a period of 24 hours; thus the tablets object of the present invention are suitable for a once a day administration.

4 Claims, 2 Drawing Sheets

PROGRAMMED RELEASE TABLETS CONTAINING NAPROXEN

FIELD OF THE INVENTION

This application relates to antiinflammatory agents and more specifically to compositions intended for controlled release.

BACKGROUND OF THE INVENTION

The man skilled in the art well knows the problems connected with the repeated administrations of drugs. Apart from the trouble and the discomfort, mostly psychological, which the patient can experience when he has to recollect of taking that determinate medicine three or four times a day, as it happens, for instance, with paracetamol, it must be borne in mind that, from the point of view of the absorption kinetics, a repeated administration is responsible of very high hematic levels of the drug which repeatedly occur in the organism of the patient, with a remarkable increase in the possibility of side effects.

The conventional pharmaceutical formulations, tablets and capsules, generally contain from 250 to 500 mg of naproxen and are administered from two to three times a day producing very high hematic levels of the drug in the first hours subsequently to the administration. Afterwards the hematic levels have a sudden decrease and go down the therapeutically useful values. At the subsequent administration, a new very high peak takes place followed by a further sudden lowering.

This swinging development is disadvantageous because the initial overdosage strengthens the undesired side effects, while the subsequent quick lowering of the therapeutically effective hematic levels reduces the therapeutic action of the drug.

In the literature some methodologies are described, generically called <<retard>> or <<controlled release>>, by means of which the number of administrations of naproxen can be reduced, also once a day, while keeping unaltered its therapeutic effectiveness along the time: and avoiding the formation of too high peaks of hematic levels.

English patent GB 2,132,887 describes pharmaceutical formulations containing naproxen made by granules coated by a film of cellulose acetate phthalate and by a plasticizer substance like castor oil or dibutyl or diethyl phthalates. These coated granules, whose diameter is comprised between 0.4 and 1 mm, are subsequently transformed into tablets and capsules.

English patent GB 2,202,143 describes spheroids whose diameter is comprised between 0.5 and 2.5 mm where the drug disperses in a microcrystalline cellulose matrix.

International publication WO 8700044 describes controlled release tablets in which the speed of the drug's release takes place on the basis of the different types of used hydroxypropylmethylcelluloses.

U.S. Pat. No. 4,571,333 and U.S. Pat. No. 4,803,079 describe controlled release tablets containing from 500 to 1,200 mg of naproxen and from 4% to 9% by weight of hydroxypropylmethylcellulose having a molecular weight comprised between 80,000 and 130,000 Daltons. These tablets, also containing excipients and lubricating agents, are suitable to be administered once a day.

Finally the European publication EP 0,255,002 describes programmed release pharmaceutical formulations, tablets, capsules and granulates containing from 375 to 750 mg of naproxen suitable for an once a day administration.

The programmed release is obtained by mixing a granulate having immediate release containing from 30% to 70% of the entire amount of the active principle together with binding, disintegrating and lubricating agents and a granulate having controlled release containing from 30% to 70% of the entire amount of the active principle together with retarding agents.

The pharmaceutical formulations described in the present invention represent an improvement of the invention described in the European publication EP 0,255,002, since the utilization of a different technology in preparing the granulate having controlled release and the addition of a disintegrating agent exterior to the granulates produce economical and industrial advantages combined with an excellent bioavailability and a speed in reaching the hematic therapeutic levels greater than that obtained in the cited European publication. This fact is so surprising and unforeseeable because the amount of naproxen present in the granulate having an immediate release is comprised between 5% and 28% in the tablets object of the present invention, while in the formulations described in European publication 0,255,002 this amount is meaningfully greater, being comprised between 30% and 70%.

Figure 1:
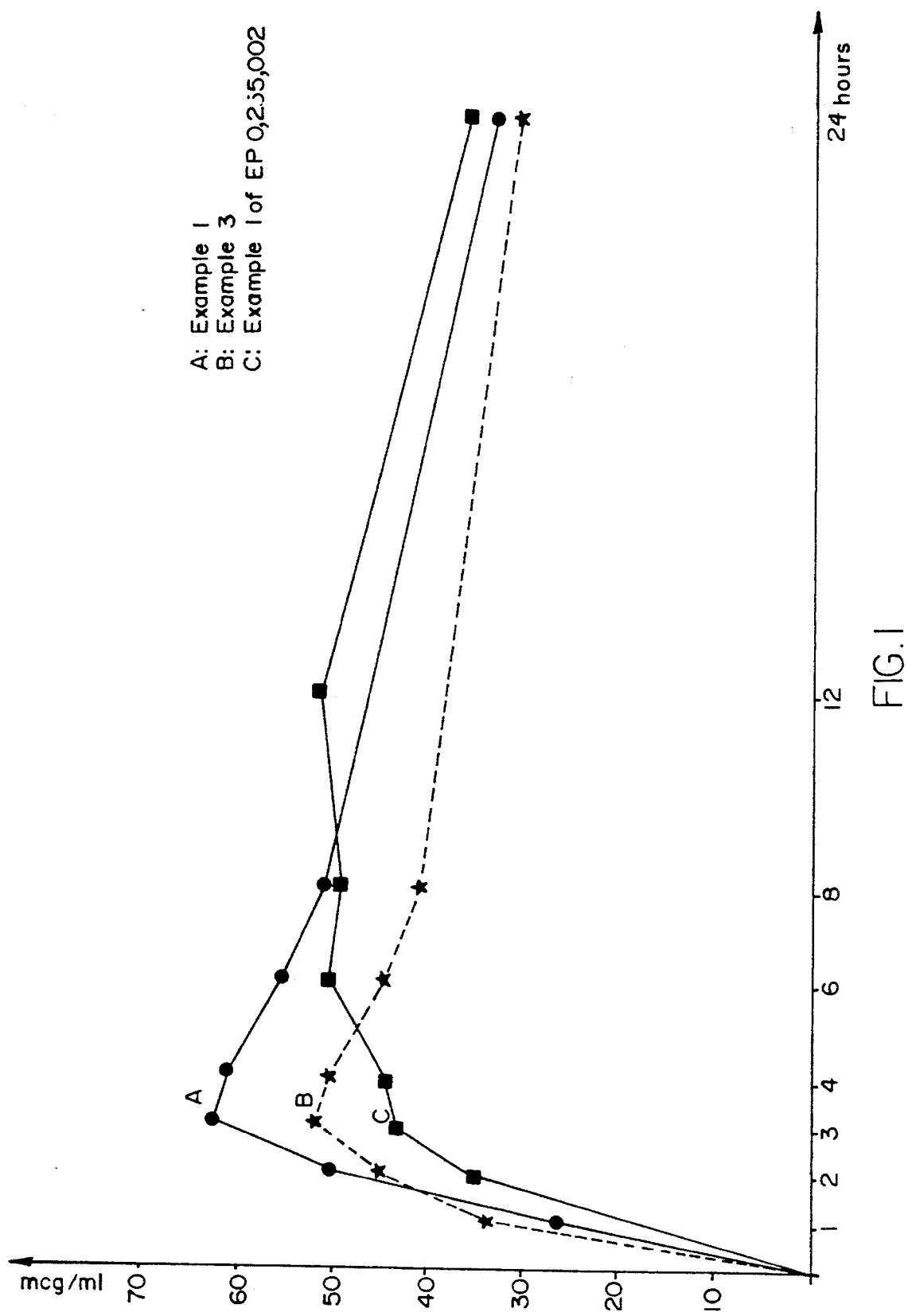
FIG. 1 shows that the desired hematic therapeutic level is reached much faster with the compositions according to the present invention, compared with the reference, EP 0,255,002, in spite of the fact that the amount of naproxen in the reference is more than double.

A pharmacokinetic test carried out on six healthy volunteers, to whom tablets of 750 mg prepared as in Examples 1 and 3 were administered, showed a quicker reaching of the therapeutic effective concentration with respect to the tablets of 750 mg described in Example 1 of EP 0,255,002 as clearly demonstrated in the following Table 1 and FIG. 1.

TABLE 1

Hematic levels of naproxen
expressed as mcg/ml of human plasma
(average of 6 values)

| Times of drawing (hours) | Example 1 | Example 3 | Example 1 EP 0,255,002 |
|---|---|---|---|
| 1 | 26.4 | 33.5 | n.d. |
| 2 | 50.2 | 45.3 | 35.7 |
| 3 | 62.6 | 51.9 | 42.8 |
| 4 | 61.1 | 50.5 | 44.3 |
| 6 | 55.4 | 44.9 | 50.1 |
| 8 | 51.0 | 41.7 | 48.4 |
| 12 | n.d. | n.d. | 52.8 |
| 24 | 33.4 | 31.4 | 38.1 |

Remarkable economic and industrial advantages, brought by the new production process of the pharmaceutical formulations object of the invention based on the granulation by dry compacting powders both for the granulate having immediate release and for the granulate having controlled release, join this therapeutic advantage.

The first advantage consists of the fact that this process allows to obtain a controlled release granulate that can be used just so in the production of the final pharmaceutical forms, without the necessity to select and reassemble the particle size fractions as it happens in the production process of the controlled release granulate as described in EP 0,255,002.

The second advantage consists of the avoiding solvents and drying ovens necessary for the wet-granulation of the controlled release granulate described in EP 0,255,002.

The third advantage consists of the rationalization of production systems because the same system can produce both the immediate and the controlled release granulate unlike what happens in the process described in EP 0,255,002 that requires two different types of systems.

Therefore the new process furnishes pharmaceutical formulations excellent under a therapeutic point of view having industrial costs definitely lower than those necessary for the production process of the pharmaceutical formulations described in EP 0,255,002 as regards solvents, energy, systems and times.

DESCRIPTION OF THE INVENTION

The object of the present invention consists of programmed, immediate and delayed release tablets, to be administered by oral route, containing from 500 to 1,200 mg of naproxen, drug endowed with antiinflammatory, analgesic and antipyretic activity.

The tablets object of the present invention are made by a mixture of an immediate release granulate, a controlled release granulate and a disintegrating agent. In this way, by suitably selecting both the kind and the amount of the disintegrating agent and excipients to be used in the manufacture of the two granulates and the weight ratio between the components of the mixture, it is possible to obtain tablets having an immediate therapeutical activity which protracts along 24 hours, being therefore suitable for an once a day administration.

We have found that the better therapeutical result is obtained with tablets where naproxen is present in the immediate release granulate from 5% to 28% of the entire amount of naproxen, in the controlled release granulate from 72% to 95% of the entire amount of naproxen and the amount of the disintegrating agent added to the mixture of the two granulates is comprised between 2% and 10% of the entire amount of the tablet.

The immediate release granulate is prepared by dry granulating naproxen with suitable adjuvant agents like binding, disintegrating and lubricating agents. Naproxen is suitably mixed with the binding, disintegrating and lubricating agents and the resultant mixture is sprayed with ethyl alcohol in an amount of 1.7% in weight with respect to the mixture weight and then is submitted to compactation and subsequently to a sifting on a sieve having meshes comprised between 0.6 and 2 mm, preferably between 1 and 1.6 mm.

Polyvinylpyrrolidone, carboxymethylcellulose, microcrystalline cellulose, lactose, saccharose, mannitol, gumarabic, pectin and gelatin can be advantageously used as binding agents.

Starch, sodium starch glycolate, alginates and reticulated polyvinylpyrrolidone can be advantageously used as disintegrating agents. Talc, magnesium stearate, stearic acid and silica gel can be used as lubricating agents. Polyvinylpyrrolidone, lactose, maize starch, sodium starch glycolate and magnesium stearate are the preferred adjuvants in the fulfillment of the present invention. The granulate having a controlled release is prepared by dry granulating the mixture of naproxen together with the retarding agents and sifting on a sieve having meshes comprised between 0.6 and 2 mm, preferably between 1 and 1.6 mm.

Many retarding agents can be advantageously used; they are selected among ethylcellulose, methylcellulose, polyvinylacetate, methacrylic acid esters, cellulose acetate, fatty alcohols containing from 12 to 32 carbon atoms, glyceric esters of fatty acids containing from 10 to 22 carbon atoms, like the mono- and di-stearate of glycerile, esters or fatty acids and alcohols having from 12 to 31 carbon atoms, paraffin, natural waxy substances like beeswax, unbleached wax, candelilla wax, carnauba wax, sealing wax, spermaceti, ozokerite and hydrogenated vegetable oils like hydrogenated castor oil, hydrogenated peanut oil, hydrogenated cotton seed oil and mixtures thereof. Methylcellulose, ethylcellulose, hydrogenated vegetable oils and mixtures thereof are the retarding agents preferred in the fulfillment of the present invention.

The two granulates are mixed in such weight ratios that the naproxen contained in the tablet belongs to the immediate release granulate for a percentage comprised between 5% and 28% of the entire active principle and to the controlled release granulate for a percentage comprised between 72% and 95%.

In its turn, the immediate release granulate contains from 60% to 70% of active principle, from 20% to 30% of binding agents, from 8% to 12% of disintegrating agents and from 0.2% to 1% of a lubricating agent, while the controlled release granulate contains from 60% to 70% of active principle and from 30% to 40% of a retarding agent or of a mixture of retarding agents.

In a preferred aspect of the invention, the composition of the granulates is as follows:

a) Immediate release granulate from 60% to 70% of naproxen, from 17% to 23% of lactose, from 3% to 7% of polyvinylpyrrolidone, from 4% to 8% of maize starch, from 3% to 6% of sodium starch glycolate, from 0.2% to 0.5% of magnesium stearate.

b) Controlled release granulate from 60% to 70% of naproxen, from 20% to 30% of hydrogenated castor oil, from 6% to 12% of ethylcellulose.

The tablets are prepared by carefully mixing the two types of granulate with the disintegrating agent and then submitting the resultant mixture to compression through a tablet compressing machine.

The tablets contain from 16% to 18% by weight of the immediate release granulate, from 75% to 80% by weight of the controlled release granulate and from 5% to 7% by weight of disintegrating agent according to a preferred aspect of the invention.

Reticulated polyvinylpyrrolidone is the disintegrating agent preferred in the fulfillment of the present invention.

Some examples of tablets obtained according to that above described are reported in order to illustrate the invention.

These examples, and also the example related to the pharmacokinetic test carried out on man, are not to be interpreted as a limitation of the invention itself.

EXAMPLE 1

| Tablets containing 750 mg of naproxen | |
|---|---|
| Composition of the immediate release granulate in mg/tablet | |
| naproxen | 135 |
| lactose | 40.3 |
| polyvinylpyrrolidone | 8.2 |

-continued

| Tablets containing 750 mg of naproxen | |
|---|---|
| maize starch | 13.6 |
| sodium starch glycolate | 8.2 |
| magnesium stearate | 0.55 |
| Composition of the controlled release granulate in mg/tablet | |
| naproxen | 615 |
| hydrogenated castor oil | 233.7 |
| ethylcellulose | 73.8 |

The immediate release granulate is prepared by mixing the active principle with excipients, spraying the mixture with 1.7% in weight of atomized ethyl alcohol, dry granulating it and sifting the granules on a sieve having meshes of 1.25 mm.

The controlled release granulate is prepared by mixing the active principle with retarding agents, dry granulating the mixture and sifting the granules on a sieve having meshes of 1.25 mm.

The two granulates are mixed together with reticulated polyvinylpyrrolidone in an amount of 68 mg/tablet and the mixture is tabletted through a compressing machine.

EXAMPLE 2

| Tablets containing 500 mg of naproxen | |
|---|---|
| Composition of the immediate release granulate in mg/tablet | |
| naproxen | 125 |
| lactose | 37.3 |
| polyvinylpyrrolidone | 7.6 |
| maize starch | 12.6 |
| sodium starch glycolate | 7.6 |
| magnesium stearate | 0.5 |
| Composition of the controlled release granulate in mg/tablet | |
| naproxen | 375 |
| hydrogenated castor oil | 142.5 |
| ethylcellulose | 45 |

The tablets are obtained as described in Example 1 adding to the mixture of the two granulates an amount of 46 mg/tablet of reticulated polyvinylpyrrolidone.

EXAMPLE 3

Tablets containing 750 mg of naproxen

The tablets are prepared with the same composition and method described in Example 1 with the only change that the two granulates are obtained using a sieve having meshes of 1.6 mm.

EXAMPLE 4

Pharmacokinetic test on man

Pharmacokinetic tests have been carried out on man in order to verify the effectiveness, both immediate and in the long time, of the above described tablets. The tests have been carried out administering to each of six healthy volunteers a tablet containing 750 mg of naproxen. Tablets prepared as described in Example 1 (A) have been administered in the first test and tablets prepared as described in Example 3 (B) have been administered in the second test, carried out 15 days after, following the same procedures and on the same healthy volunteers.

Figure 2:
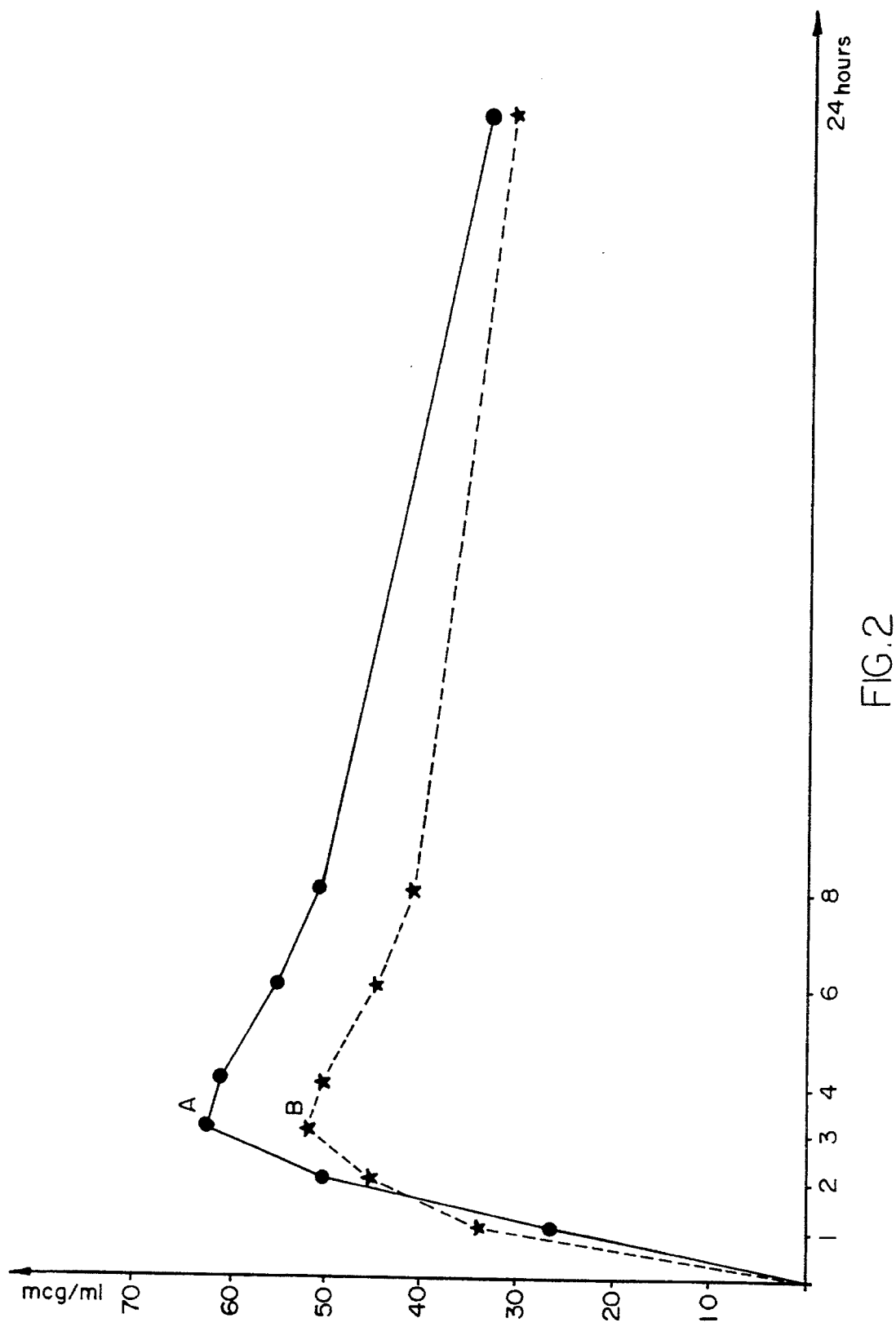
FIG. 2 shows the hematic levels in man achieved over a period of 24 hours with the compositions according to the present invention.

At fixed times, 1, 2, 3, 4, 6, 8 and 24 hours after the administration of the tablets, a blood drawing has been carried out and the quantity of naproxen has been determined on plasma obtained with the addition of EDTA. The analytical determination has been carried out by means of the HPLC-method using a WATERS-apparatus endowed with spectrophotometer detector mod. 484 placed at 272 nm. The values reported in the following Table 2 and FIG. 2 have been calculated over the mean of the values of the single values of the six healthy volunteers.

TABLE 2

Hematic levels of naproxen
expressed as mcg/ml of human plasma
(average of 6 values)

| Times of drawing (hours) | Example 1 (A) | Example 3 (B) |
|---|---|---|
| 1 | 26.4 | 33.5 |
| 2 | 50.2 | 45.3 |
| 3 | 62.6 | 51.9 |
| 4 | 61.1 | 50.5 |
| 6 | 55.4 | 44.9 |
| 8 | 51.0 | 41.7 |
| 24 | 33.4 | 31.4 |

What is claimed:

1. A programmed release tablet containing from 500 to 1,200 mgs. of naproxen, said tablet being prepared by the steps of 1) preparing an immediate release dry granulate containing from 5% to 28% of the entire amount of naproxen in the tablet in admixture with a binding agent, a disintegrating agent and a lubricating agent; said binding agent being a member selected from the group consisting of polyvinylpyrrolidone and lactose and mixtures thereof, said disintegrating agent being a member selected from the group consisting of starch and sodium starch glycolate and mixtures thereof, said lubricating agent being magnesium stearate, 2) preparing a controlled release dry granulate containing from 72% to 95% of the entire amount of naproxen in the tablet in admixture with a retarding agent, said retarding agent being a member selected from the group consisting of ethylcellulose, hydrogenated castor oil and mixtures thereof.

3) mixing said immediate release granulate from step 1) with said controlled release granulate from step 2) to obtain a mixture;

4) adding reticulated polyvinyl pyrrolidone in an amount between 2% and 10% of the entire amount of the tablet as a disintegrating agent to said mixture from step 3) to obtain said mixture having said reticulated polyvinylpyrrolidone applied thereon and 5) compressing said mixture from step 4) to obtain a tablet.

2. The tablet according to claim 1 wherein the two granulates are obtained by dry compaction and are sifted on sieves having meshes comprised between 0.6 and 2 mm.

3. The tablet according to claim 2 wherein the sieve meshes comprised between 1 and 1.6 mm.

4. The tablet according to claim 1 which contains 750 mg of naproxen, obtained from a mixture having the following composition for each tablet:

Immediate release granulate
naproxen 135 mg
lactose 40.3 mg
polyvinylpyrrolidone 8.2 mg
maize starch 13.6 mg
sodium starch glycolate 8.2 mg
magnesium stearate 0.55 mg

| Controlled release granulate | |
|---|---|
| naproxen | 615 mg |
| hydrogenated castor oil | 233.7 mg |
| ethyl cellulose | 73.8 mg |
| Disintegrating agent | |
| reticulated polyvinylpyrrolidone | 68 mg |

* * * * *